United States Patent [19]

Hayes

[11] Patent Number: 4,491,586
[45] Date of Patent: Jan. 1, 1985

[54] AMINE DERIVATIVES

[75] Inventor: Roger Hayes, Potters Bar, England

[73] Assignee: Glaxo Group Limited, London, England

[21] Appl. No.: 450,479

[22] Filed: Dec. 16, 1982

[30] Foreign Application Priority Data

Jun. 5, 1980 [GB] United Kingdom ............... 8018403
Aug. 27, 1980 [GB] United Kingdom ............... 8027742

[51] Int. Cl.³ .................. A61K 31/445; C07D 211/14
[52] U.S. Cl. .................................... 424/267; 424/246; 424/248.56; 424/263; 424/274; 424/244; 546/231; 546/332; 546/102; 546/105; 546/107; 548/569; 544/162; 544/59; 564/237; 260/239 B
[58] Field of Search ............... 546/231, 332, 102, 105, 546/107; 548/569; 544/59, 162; 564/237; 260/239 B; 424/326, 330, 321, 244, 246, 248.56, 263, 267, 274

[56] References Cited

U.S. PATENT DOCUMENTS 4,128,658 12/1978 Price et al. ........................ 424/285
4,239,769 12/1980 Price et al. ........................ 424/274

FOREIGN PATENT DOCUMENTS 867105 11/1978 Belgium ............................ 424/274
856106 11/1978 Belgium ............................ 424/274
2006771 5/1979 United Kingdom ............. 424/274
1604674 12/1981 United Kingdom ............. 546/231
1604675 12/1982 United Kingdom ............. 546/231

Primary Examiner—Robert T. Bond
Attorney, Agent, or Firm—Bacon & Thomas

[57] ABSTRACT

The invention provides compounds of the general formula (I)

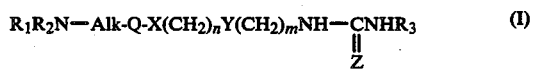

and physiologically acceptable salts, hydrates and bioprecursors thereof in which the substituents are defined in the specification.

The compounds of formula (I) show pharmacologically activity as selective histamine $H_2$-antagonists.

7 Claims, No Drawings

AMINE DERIVATIVES

This invention relates to novel amine derivatives having action on histamine receptors, to process for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore, the compounds antagonise the effect of histamine on the contraction frequency of isolated guinea pig right atrium but do not modify histamine induced contractions of isolated gastro-intestinal smooth muscle which are mediated via $H_1$-receptors.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone, or in combination with other active ingredients in the treatment of allergic and inflammatory conditions of the skin.

The present invention provides compounds of the general formula (I)

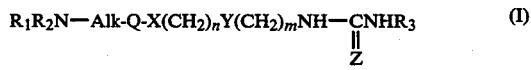

and physiologically acceptable salts, hydrates and bioprecursors thereof in which $R_1$ represents hydrogen, cycloalkyl, aralkyl, trifluoroalkyl, heteroaralkyl or $C_{1-6}$ alkyl substituted by cycloalkyl or a $C_{1-16}$ straight or branched saturated or unsaturated alkylene chain optionally substituted by a hydroxy, amino, alkylamino, dialkylamino, ester ($-CO_2R_6$ where $R_6$ is a $C_{1-3}$ alkyl group) or carboxamide ($CONH_2$) group, or $R_1$ represents a $C_{1-16}$ straight or branched saturated or unsaturated alkylene chain interrupted by an oxygen atom, sulphur atom, sulphoxide, sulphone, amide ($-CONH-$ or $-NHCO-$) or ester ($-COO-$ or $-OCO-$) group with the proviso that when the alkylene chain is interrupted by an oxygen or sulphur atom, or the sulphoxide, $-CONH-$ or $-COO-$ group then there must be at least two carbon atoms between that group and the nitrogen atom to which the group $R_1$ is attached;

$R_2$ represents hydrogen or a $C_{1-4}$ alkyl group; or $R_1$ and $R_2$ together with the nitrogen atom to which they are attached form a 5–10 membered ring which may be saturated or may contain at least one double bond, may be unsubstituted or may be substituted by one or more $C_{1-3}$ alkyl groups e.g. methyl or a hydroxy group and/or may contain another heteroatom, e.g. oxygen or sulphur;

Alk represents a straight or branched alkylene chain of 1 to 6 carbon atoms, preferably 1 to 4 carbon atoms;

Q represents a furan or thiophen ring in which incorporation into the rest of the molecule is through bonds at the 2- and 5- positions, the furan ring optionally bearing a further substituent $R_4$ adjacent to the group $R_1R_2-N-Alk-$, or Q represents a benzene ring in which incorporation into the rest of the molecule is through bonds at the 1- and 3- or 1- and 4- positions;

$R_4$ represents halogen, or $C_{1-4}$ alkyl which may be substituted by hydroxy or $C_{1-4}$ alkoxy;

X and Y, which may be the same or different, each represent oxygen or sulphur, or one of X and Y represents $-CH_2-$ and the other represents oxygen or sulphur;

n and m, which may be the same or different, each represent 2 or 3;

$R_3$ represents hydrogen, alkyl, alkenyl, alkynyl, aralkyl or alkoxyalkyl; and

Z represents $CHNO_2$ or $NR_5$ where $R_5$ is nitro, cyano, alkylsulphonyl or arylsulphonyl.

The term "alkyl" as a group or part of a group means that the group is straight or branched and has unless otherwise stated preferably 1 to 6 carbon atoms, and in particular 1 to 4 carbon atoms, e.g. methyl or ethyl, and the term "alkenyl" means that the group has preferably 3 to 6 carbon atoms. The term "cycloalkyl" means that the group has 3 to 8 carbon atoms. The term "aryl" as a group or part of a group preferably means phenyl or substituted phenyl, for example phenyl substituted with one or more $C_{1-3}$ alkyl or $C_{1-3}$ alkoxy groups or halogen atoms. The term "heteroaralkyl" as applied to the group $R_1$ means that the group is made up of a heterocyclic part which is a mono or bicyclic, unsaturated, substituted or unsubstituted ring containing from 5 to 10 atoms selected from carbon, oxygen, nitrogen and sulphur, and an alkyl part which is a straight or branched alkylene chain with 1 to 4 carbon atoms, the heterocyclic ring being linked to the alkylene chain either through carbon or nitrogen and when the heterocyclic ring is substituted the substituent being chosen from $C_{1-3}$ alkyl, $C_{1-3}$ alkoxy, hydroxy, aminoalkyl and halogen. If the heterocyclic ring is monocyclic it preferably contains 5 or 6 members and if it is bicyclic it preferably contains 9 or 10 members. The term "unsaturated" in relation to an alkylene chain means that it contains at least one $-C=C-$ or $-C\equiv C-$ grouping.

The invention includes the compounds of formula (I) in the form of physiologically acceptable salts with inorganic and organic acids. Particularly useful salts include hydrochlorides, hydrobromides and sulphates, methanesulphonates, acetates, maleates, succinates, tartrates, benzoates, citrates and fumarates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The term bioprecursors as used herein means compounds which have a structure different to that of the compounds of formula (I) but which, upon administration to an animal or human being, are converted in the body into a compound of formula (I).

The compounds according to the invention, preferably in the form of a salt, may be formulated for administration in any convenient way and the invention includes within its scope pharmaceutical compositions containing at least one compound according to the invention, adapted for use in human or veterinary medicine. Such compositions may be formulated in a conventional manner using one or more pharmaceutically acceptable carriers or excipients. Such compositions may also contain if required other active ingredients, e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg to 2 g per day, preferably 5 to 500 mg per day dependent upon the condition of the patient.

Examples of suitable meanings for the groups $R_1$, $R_2$ and $R_4$ are as follows:

$R_1$: alkyl containing up to 16 carbon atoms (e.g. methyl, ethyl, propyl, butyl, pentyl, hexyl, heptyl or decyl), and optionally containing an ester or amide grouping, $C_{5-7}$ cycloalkyl (e.g. cyclopentyl, cyclohexyl or cycloheptyl), alkenyl (e.g. allyl or 3,3-dimethylallyl), aralkyl (e.g. phenylalkyl such as benzyl or phenethyl), $C_{1-4}$ alkyl substituted by a trifluoromethyl group (e.g. 2,2,2-trifluoroethyl), hydroxy $C_{2-4}$ alkyl (e.g. 3-hydroxypropyl), $C_{1-3}$ alkoxy $C_{2-4}$ alkyl (e.g. methoxyethyl or ethoxyethyl), or di-$C_{1-3}$ alkylaminoalkyl (e.g. dimethylaminoethyl, diethylaminoethyl or dimethylaminopropyl), or heteroaralkyl where the heterocyclic portion represents for example a furyl, thienyl, pyrrolyl, pyridinyl, pyrimidinyl, triazinyl, oxazolyl, triazolyl, thiazolyl, isoquinolinyl, quinolinyl or indolyl ring and the alkylene portion is for example methylene, ethylene or propylene;

$R_2$: hydrogen or $C_{1-4}$ alkyl (e.g. methyl or ethyl); or $R_1R_2N$ may represent a 5–8 membered ring optionally containing one double bond and/or substituted by one or two $C_{1-3}$ alkyl (e.g. methyl) groups or a hydroxy group and/or containing an oxygen or sulphur atom (e.g. pyrrolidino, piperidino, hexamethylenimino, heptamethylenimino, tetrahydropyridino, 4-hydroxypiperidino, 4-$C_{1-3}$ alkylpiperidino (e.g. 4-methylpiperidino), morpholino, 2,6-di-$C_{1-3}$ alkylmorpholino (e.g. 2,6-dimethylmorpholino) or thiomorpholino);

$R_4$: bromine atom or a $C_{1-3}$ alkyl group (e.g. methyl, ethyl or isopropyl) or a $C_{1-3}$ alkoxy $C_{1-3}$ alkyl group (e.g. methoxymethyl).

Examples of suitable meanings for $R_3$ and Z are as follows:

$R_3$: hydrogen, $C_{1-4}$ alkyl (e.g. methyl or ethyl) or $C_{1-3}$ alkoxy $C_{2-4}$ alkyl (e.g. methoxyethyl) CHNO$_2$ or NR$_5$ where R$_5$ is nitro, cyano or $C_{1-4}$ alkylsulphonyl (e.g. methylsulphonyl). The group Alk may be for example the group $(CH_2)_p$ where p is 1, 2, or 3.

In particular the groups $R_1$ and $R_2$ may have meanings as follows:

$R_1$: $C_{1-7}$ alkyl (e.g. methyl, propyl, butyl, isobutyl, or heptyl), $C_{1-4}$ alkyl substituted by a trifluoromethyl group (e.g. 2,2,2-trifluoroethyl), $C_{2-4}$ alkyl substituted by hydroxy or a di $C_{1-3}$ alkylamino group (e.g. 3-hydroxypropyl or dimethylaminoethyl), $C_{5-7}$ cycloalkyl (e.g. cyclohexyl), alkenyl (e.g. allyl), phenyl $C_{1-3}$ alkyl (e.g. benzyl), or a heteroaryl $C_{1-3}$ alkyl group where the heteroaryl ring is 5 or 6 membered and contains one heteroatom (e.g. 2-furylmethyl);

$R_2$: hydrogen or methyl; or $R_1R_2N$ may represent a 5 to 7 membered ring optionally containing a double bond or an alkyl (e.g. methyl substituent (e.g. piperidino, 4-methylpiperidino pyrrolidino, hexamethylenimino or tetrahydropyridino.

In particular the groups $R_3$ and Z may have meanings as follows:

$R_3$: hydrogen or $C_{1-3}$ alkyl (e.g. methyl)

Z: CHNO$_2$ or NR$_5$ where R$_5$ is cyano, nitro or methylsulphonyl.

Alk is particularly a methylene or ethylene group, more particularly methylene.

The group Q is preferably a benzene ring in which incorporation into the rest of the molecule is through bonds at the 1- and 3-position.

One of X and Y is preferably oxygen and the other is preferably oxygen or methylene.

n and m are preferably both two.

The group Z is preferably CHNO$_2$ and $R_3$ is more particularly alkyl (e.g. methyl).

A preferred group of compounds of formula (I) are those of formula (II)

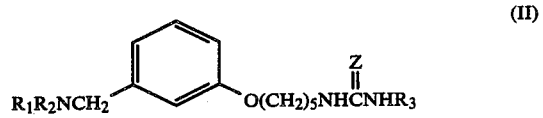

(II)

in which $R_1R_2N$ forms a pyrrolidino, piperidino, hexamethylenimino, tetrahydropyridino or 4-methylpiperidino group; Z represents CHNO$_2$ or NR$_5$ where R$_5$ is methylsulphonyl, more preferably CHNO$_2$; and $R_3$ represents hydrogen, $C_{1-4}$ alkyl or $C_{1-3}$ alkoxy $C_{2-4}$ alkyl, more preferably $C_{1-4}$ alkyl e.g. methyl.

A particularly preferred compound is N-[5-[3-(1-piperidinylmethyl)phenoxy]pentyl]-N$^1$-methyl-2- nitro-1,1-ethenediamine and its physiologically acceptable salts.

According to one aspect the invention provides compounds of formula (I) in which R₁ represents hydrogen, cycloalkyl, aralkyl, trifluoroalkyl, heteroaralkyl or $C_{1-6}$ alkyl substituted by cycloalkyl, amino, alkylamino or dialkylamino;

or R₁ represents a $C_{1-16}$ straight or branched saturated or unsaturated alkylene chain which may be optionally substituted by a hydroxy, ester ($CO_2R_6$ where $R_6$ is a $C_{1-3}$ alkyl group) or carboxamide ($CONH_2$) group; or R₁ represents a $C_{1-16}$ straight or branched saturated or unsaturated alkylene chain interrupted by an oxygen atom, sulphur atom, sulphoxide, sulphone, amide (—CONH— or —NHCO—) or ester (—COO— or —OCO—) group, with the proviso that when the alkylene chain is interrupted by an oxygen or sulphur atom, or the sulphoxide, —CONH— or —COO— group then there must be at least two carbon atoms between that group and the nitrogen atom to which the group R₁ is attached:

R₂ represents hydrogen or a $C_{1-4}$ alkyl group;

or R₁ and R₂ together with the nitrogen atom to which they are attached form a 5-10 membered ring which may be saturated or may contain at least one double bond, may be unsubstituted or may be substituted by one or more $C_{1-3}$ alkyl groups or a hydroxy group and/or may contain another heteroatom.

It will be appreciated in the methods for the preparation of the compounds of formula (I) given below that for certain reaction steps it may be necessary to protect various reactive substituents in the starting materials for a particular reaction and subsequently to remove the protecting group. Such protection and subsequent deprotection may be particularly pertinent when R₁ and/or R₂ and/or R₃ are hydrogen. Standard protection and deprotection procedures can be employed.

For example formation of phthalimide (in the case of primary amines), benzyl, benzyloxycarbonyl, or trichloroethoxycarbonyl derivatives. Subsequent cleavage of the protecting group is achieved by conventional procedures. Thus a phthalimide group may be cleaved by treatment with a hydrazine e.g. hydrazine hydrate or a primary amine for example methylamine, benzyl or benzyloxycarbonyl derivatives may be cleaved by hydrogenolysis in the presence of a catalyst, e.g. palladium, and trichloroethoxycarbonyl derivatives may be cleaved by treatment with zinc dust.

In describing the processes which may be used for preparing the compounds of formula (I) or intermediates useful in the preparation thereof, any of R₁ to R₅, Alk, Q, X, Y, Z, n and m are as defined in formula (I) unless otherwise stated.

Compounds of formula (I) may be made by reacting an amine of the formula $R_6NH_2$ (III) with a compound of general formula (IV)

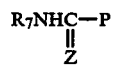  (IV)

wherein one of the groups R₆ and R₇ represents the group $R_1R_2NAlkQX(CH_2)_nY(CH_2)_m$- and the other represents the group R₃, and P is a leaving group such as halogen, thioalkyl (preferably thiomethyl) or alkoxy.

Compounds of formula (IV) may be prepared by reacting the amine (III) with a compound of formula (V)

  (V)

where P is as defined in formula (IV).

The above reactions may be effected in the absence or presence of a solvent e.g. ethanol, dioxan, acetonitrile, water or aqueous ethanol at a temperature from ambient to reflux. In the absence of a solvent the reaction may be carried out by heating a mixture of the reactants at for example 100°-120° C.

Amines of the formula (III) where R₆ represents the group $R_1R_2NAlkQX(CH_2)_nY(CH_2)_m$— may be made by methods analogous to those described in German Offenlegungsschrifts Nos. 2,734,070, 2,821,410 and 2,821,409. For example, amines of formula (III) in which X is oxygen or sulphur may be prepared by reacting a compound of formula (VI)

  , (VI)

with the phthalimide derivative (VII)

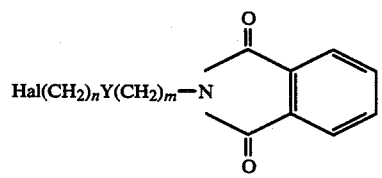  (VII)

where Hal is chlorine or bromine, in the presence of a base followed by removal of the phthalimide protecting group.

Amines of formula (III) in which X is —CH₂— may be prepared by reacting a compound of formula (VIII) with a compound of formula (IX)

  (VIII)

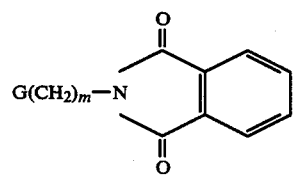  (IX)

where either J is a leaving group e.g. halogen and G is a hydroxyl or thiol group, or J is a hydroxyl or thiol group and G is a leaving group e.g. halogen. The reaction is carried out in the presence of a base e.g. sodium hydride or potassium carbonate, in a solvent such as dimethylformamide or acetone respectively, to give an intermediate of formula (X)

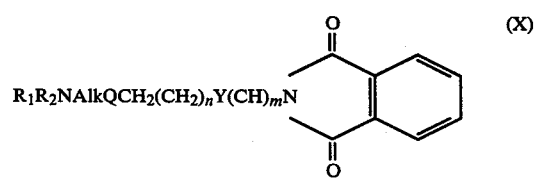  (X)

from which the amine (III) in which X is —CH₂— may be formed by cleavage of the phthalimide protecting group.

Where the product of any of the above processes is a free base and a salt is required, the salt may be formed in a conventional manner. Thus, for example, a generally convenient method of forming the salts is a mix appropriate quantities of the free base and the acid in an appropriate solvent (s), e.g. an alcohol such as ethanol or an ester such as ethyl acetate.

The invention is illustrated by the following examples. In the following examples t.l.c. refers to thin layer chromatography carried out on silica using unless otherwise stated one of the following solvent systems:
A: ethyl acetate/water/isopropanol/0.88 ammonia (25:8:15:2)
B: methanol/0.88 ammonia (80.1).

Column chromatography was carried out on silica using methanol as eluant unless otherwise stated.

PREPARATION 1

6-[3-(1-Piperidinylmethyl)phenoxy]hexanamine

A suspension of 3-(1-piperidinylmethyl)phenol (3.9 g) and sodium hydride (0.49 g) in dry dimethylformamide (70 ml) was stirred at 25° for 6 h. 2-(6-Bromohexyl)1H-isoindole-1,3-(2H)-dione (6.4 g) was added and the solution was stirred at 25° for 16 h. The mixture was poured onto water and extracted with ethyl acetate. The organic extract was evaporated to leave a dark brown oil (8.6 g) which was used without further purification.

A solution of the oil and hydrazine hydrate (1.5 g) in ethanol (200 ml) was heated at reflux for 8 h. Ether was added to the cooled solution and the precipitate was removed by filtration. The filtrate was distilled to give the title compound as a pale yellow oil (2.3 g) b.p. 170°/0.1 mm.

The following compounds were similarly prepared from 3-(1-piperidinylmethyl)phenol[A]and the corresponding 2-(halosubstituted alkyl)-1H-isoindole-1, 3-(2H)-dione.

(b) A (5.2 g) and 2-(5-Bromopentyl)-1H-isoindole-1, 3-(2H)-dione (8 g) gave 5-[3-(1-piperidinylmethyl)-penoxy]pentanamine as a colourless oil (4.3 g) b.p. 150° (0.1 mm).

(c) A (2.7 g) and 2-[2-(2-Chloroethoxy)ethyl]-1H-isoindole-1,3-(2H)-dione (3.6 g) gave 2-[2-[3-(1-piperidinylmethyl)phenoxy]ethoxy]ethanamine as an oil (2 g), b.p. 180° (0.1 mm).

EXAMPLE 1

N-Methyl-$N^1$-[2-[2-[3-(1-piperidinylmethyl)phenoxy]ethoxy]ethyl]-2-nitro-1,1-ethenediamine A solution of 2-[2-[3-(1-piperidinylmethyl) phenoxy]ethoxy]ethanamine (0.4 g) and N-methyl-1-methylthio-2-nitro-etheneamine (0.24 g) in water (20 ml) and ethanol (20 ml) was stirred at 50° for 5h. The solution was diluted with water (20 ml) acidified to pH 1 with dilute hydrochloric acid and washed with ethyl acetate (2×50 ml). The aqueous solution was basified to pH 9 with potassium carbonate and extracted with ethyl acetate (3×50 ml). Evaporation of these organic extracts gave a yellow oil which solidified when triturated with cyclohexane. The solid was recrystallised from ethyl acetate (10 ml) to give the title compound as a white powder (0.17 g) m.p. 125.5°–126.5°.

Assay Found: C, 60.28; H, 7.98; N, 14.64; $C_{19}H_{30}N_4O_4$ requires: C, 60.32; H, 7,94; N, 14.81%.

EXAMPLE 2

N-[5-[3-(1-Piperidinylmethyl)phenoxy]pentyl]-$N^1$methyl-2-nitro-1,1-ethenediamine A solution of 5-[3-(1-piperidinylmethyl)-phenoxy]-pentanamine (1.0 g) and 1-methylthio-1-methylamino-2-nitroethene (0.53 g) in water (20 ml) was stirred overnight at room temperature. The water was removed in vacuo and the resulting oil triturated with ethyl acetate to give a yellow solid which was dissolved in isopropanol:ethyl acetate (75:25). Addition of ether to the solution afforded the title compound (0.16 g) as a white crystalline solid, m.p. 112°–113°.

Found: C, 61.3; H, 8.3; N, 14.0 $C_{20}H_{32}N_4O_3.1H_2O$ requires: C, 60.9; H, 8.7; N, 14.2%.

EXAMPLE 3

-N-[2-[3-[3-[(N,N-Dimethylamino)methyl]phenyl]-propoxy]ethyl]-N'-methyl-2-nitro-1-ethenediamine-.

3-[3-[2-Aminoethoxy]propyl]N,N-dimethyl-benzenemethanamine

A suspension of 3-[(N,N-dimethylamino)methyl] benzene propanol (2.5 g), potassium tertiary butoxide (0.56 g), 2-chloroethylamine hydrochloride (0.59 g) in dimethylformamide (10 ml) was stirred at 0°–5° under a nitrogen atmosphere for 24 h. The mixture was poured onto water (1 l) and extracted with ethyl acetate. The organic extract was evaporated to leave a yellow oil which was purified by column chromatography using methanol followed by methanol: 0.880 ammonia; (20:1) to give the title compound as a brown oil (73 mg). T.l.c. system B Rf 0.2.

N-[2-[3-[3-[(N,N-Dimethylamino)methyl]phenyl]-propoxy]ethyl]-N'-methyl-2-nitro-1,1-ethenediamine-.

Following the method of Example 2, 3-[3-[2-amino-ethoxy]propyl]-N,N-dimethyl-benzenemethanamine (73 mg). gave the title compound as a white powder (38 mg).

T.l.c. system B Rf 0.35
N.m.r. (CDCl$_3$)-1 to0, br.s., (1H); 2.7–3.1,m,(4H); 3.1–3.5,br.s.,(1H); 3,41,s,(1H); 6.3–6.7,m, (6H); 6.62,s,(2H); 7.20,br.s.,(3H); 7.35,m, (2H); 7.80,s,(6H); 8.12,m,(2H).

EXAMPLES OF PHARMACEUTICAL COMPOSITIONS

| TABLETS | |
|---|---|
| | mg/tablet |
| Active ingredient | 100.00 |
| Microcrystalline Cellulose BPC | 198.50 |
| Magnesium stearate BP | 1.50 |
| Compression weight | 300.00 |

The active ingredient is sieved through a 250µ sieve, blended with the excipients and compressed using 9.5 mm punches. Tablets of other strengths may be prepared by altering the compression weight and using punches to suit.

The tablets may be film coated with suitable film forming materials, e.g. methyl cellulose or hydroxypropyl methyl cellulose using standard techniques. Alternatively the tablets may be sugar coated.

| Injection for Intravenous Administration | |
| --- | --- |
| | % w/v |
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of the formula (I)

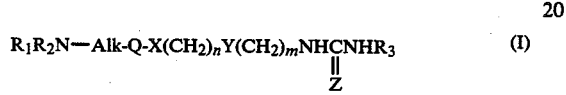

an physiologically acceptable salts and hydrates thereof in which $R_1$ represents hydrogen, $C_{3-8}$ cycloalkyl, ar $C_{1-16}$ alkyl, wherein ar is phenyl or phenyl substituted with one or more $C_{1-3}$ alkyl or $C_{1-3}$ alkoxy groups or halogen atoms; trifluoro $C_{1-6}$ alkyl, heteroaralkyl wherein the heterocyclic portion represents a furyl, thienyl, pyrrolyl, pyridinyl, pyrimidinyl, triazinyl, oxazolyl, triazolyl, or thiazolyl ring and the alkylene portion is methylene, ethylene or propylene, with the heterocyclic ring linked to the alkylene chain through either carbon or nitrogen, or $R_1$ represents $C_{1-6}$ alkyl substituted by $C_{3-8}$ cycloalkyl, or a $C_{1-16}$ straight or branched saturated or unsaturated alkylene chain optionally substituted by a hydroxy, amino, $C_{1-6}$ alkylamino, di-$C_{1-6}$ alkylamino, ester (—$CO_2R_2$ where $R_6$ is a $C_{1-3}$ alkyl group) or carboxamide ($CONH_2$) group, or $R_1$ represents a $C_{1-16}$ straight or branched saturated or unsaturated alkylene chain interrupted by an oxygen atom, sulphur atom, sulphoxide, sulphone, amide (—COHN— or —NHCO—) or ester (—COO— or —OCO—) group with the proviso that when the alkylene chain is interrupted by an oxygen or sulphur atom, or a sulphoxide, —CONH— or —COO—group then there must be at least two carbon atoms between that group and the nitrogen atom to which the group $R_1$ is attached;

$R_2$ represents hydrogen or a $C_{1-4}$ alkyl group;

or $R_1$ and $R_1$ together with the nitrogen atom to which they are attached form a pyrrolidino, piperidino, hexamethylenimino, heptamethylenimino, tetrahydropyridino, 4-hydroxypiperidino, 4-$C_{1-3}$ alkylpiperidino, 4-hydroxypiperidino, 4-$C_{1-3}$ alkylpiperidino, morpholino, 2,6-di-$C_{1-3}$ alkylmorpholino or thiomorpholino;

Alk represents a straight or branched alkylene chain of 1 to 6 carbon atoms;

Q represents a furan or thiophen ring in which incorporation into the rest of the molecule is through bonds at the 2- and 5-positions, the furan ring optionally bearing a further substituent $R_4$ adjacent to the group $R_1R_2N$- Alk-, or Q represents a benzene ring in which incorporation into the rest of the molecule is through bonds at the 1-and 3-or 1-and 4-positions;

$R_4$ represents halogen, or $C_{1-4}$ alkyl which may be substituted by hydroxy or $C_{1-4}$ alkoxy;

X and Y, which may be the same or different, each represent oxygen or sulphur, or one of X and Y represents -$CH_2$- and the other represents oxygen or sulphur;

n and m, which may be the same or different, each represents 2 or 3;

$R_3$ represents hydrogen, $C_{1-6}$ alkyl, $C_{3-6}$ alkenyl, $C_{3-6}$ alkynyl, ar $C_{1-6}$ alkyl wherein ar is phenyl or phenyl substituted with one or more $C_{1-3}$ alkyl or $C_{1-3}$ alkoxy groups or halogen atoms; or $C_{1-6}$ alkoxy $C_{1-6}$ alkyl; and Z represents $CHNO_2$.

2. A compound according to claim 9, in which the groups $R_1$, $R_2$, $R_3$, $R_4$, Z and Alk have the following meanings:

$R_1$: alkyl containing up to 16 carbon atoms and optionally containing an ester or amide grouping, $C_{5-7}$ cycloalkyl, Chd 3-6 alkenyl, ar $C_{1-6}$ alkyl, wherein ar is phenyl or phenyl substituted with one or more $C_{1-3}$ alkyl or $C_{1-3}$ alkoxy groups or halogen atoms; $C_{1-4}$ alkyl substituted by a trifluoromethyl group, hydroxy, $C_{2-4}$ alkyl, $C_{1-3}$ alkoxy $C_{2-4}$ alkyl, or di-$C_{1-3}$ alkylamino $C_{1-6}$ alkyl, or heteroaralkyl where the heterocyclic portion represents a furyl, thienyl, pyrrolyl, pyridinyl, pyrimidinyl, triazinyl, oxazolyl, triazolyl, or thiazolyl ring and the alkylene portion is methylene, ethylene or propylene;

$R_2$: hydrogen or $C_{1-4}$ alkyl; or $R_1R_2N$: may represent pyrrolidino, piperidino, hexamethylenimino, heptamethylenimino, tetrahydropyridino, 4-hydroxypiperidino, 4-$C_{1-3}$ alkylpiperidino, 4-hydroxypiperidino, 4-$C_{1-3}$ alkylpiperidino, morpholino, 2,6-di-$C_{1-3}$ alkylmorpholino or thiomorpholino group;

$R_4$: bromine atom or a $C_{1-3}$ alkyl group or a $C_{1-3}$ alkoxy $C_{1-3}$ alkyl group;

$R_3$: hydrogen, $C_{1-4}$ alkyl or $C_{1-3}$ alkoxy $C_{2-4}$ alkyl;

Z: $CHNO_2$ and the group Alk is the group $(CH_2)_p$ where p is 1,2 or 3.

3. A compound according to claim 1 in which the group Q is a benzene ring in which incorporation into the rest of the molecule is through bonds at the 1- and 3-positions; one of X and Y is oxygen and the other is oxygen or methylene; and n and m are both two.

4. A compound according to claim 1 corresponding to formula (II)

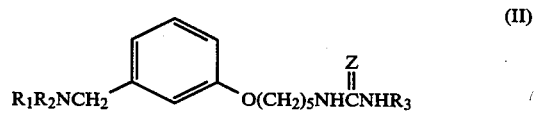

in which $R_1R_2N$ forms a pyrrolidino, piperidino, hexamethylenimino, tetrahydropyridino or 4-methylpiperidino group; Z represents $CHNO_2$ and $R_3$ represents hydrogen, $C_{1-4}$ alkyl or $C_{1-3}$ alkoxy $C_{2-4}$ alkyl.

5. A compound according to claim 1, which is N-[5-[3-(1-piperidinylmethyl)phenoxy]pentyl]-$N^1$-methyl-2-nitro-1,1-ethenediamine or a physiologically acceptable salt thereof.

6. A method of treating a condition mediated through histamine $H_2$-receptors which comprises administering to a patient an effective amount of a compound according to claim 1 to relieve said condition.

7. A pharmaceutical composition for the treatment of conditions mediated through $H_2$-receptors comprising an effective amount of at least one compound as claimed in claim 1 together with at least one pharmaceutically acceptable carrier or diluent.

* * * * *